United States Patent [19]

Dowd et al.

[11] Patent Number: 5,017,598

[45] Date of Patent: May 21, 1991

[54] NOMININE, AND INSECTICIDAL FUNGAL METABOLITE

[75] Inventors: Patrick F. Dowd; Donald T. Wicklow, both of Peoria, Ill.; James B. Gloer, Iowa City, Iowa; Brad L. Rinderknecht, Long Beach, Calif.

[73] Assignees: The United States of America, as represented by the Secretary of Agriculture, Washington, D.C.; University of Iowa Research Foundation, Iowa City, Iowa

[21] Appl. No.: 353,363

[22] Filed: May 17, 1989

[51] Int. Cl.$^5$ .................... A61K 31/40; C07D 209/12
[52] U.S. Cl. ................................... 514/415; 548/469
[58] Field of Search ........................ 548/469; 514/415

[56] References Cited

PUBLICATIONS

J. Gloer et al., J. Org. Chem., 54, 2530–2532 (1989).
C. Kurtzman et al., J. Microbiol., 53 (3), 147–158 (1987).
J. B. Gloer et al., "Antiinsectan Aflavinine Derivatives from the Sclerotia of *Aspergillus flavus,*" J. Org. Chem. 53: 5457–5460 (1988).

Primary Examiner—Mary E. Ceperley
Attorney, Agent, or Firm—M. Howard Silverstein; John D. Fado; Curtis P. Ribando

[57] ABSTRACT

A novel indole diterpene compound named "nominine" has been isolated from the sclerotia of the fungus, *Aspergillus nomius*. Nominine is characterized by the structural formula

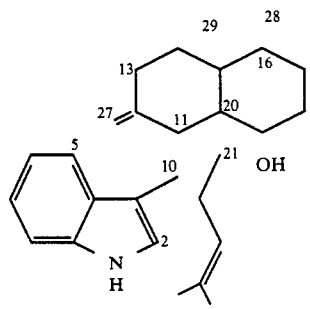

and is effective for controlling Lepidopteran and Coleopteran insect pests.

7 Claims, No Drawings

NOMININE, AND INSECTICIDAL FUNGAL METABOLITE

BACKGROUND OF THE INVENTION

1. Field of the Invention

This invention relates to a novel indole diterpene compound and its use as an insecticide for control of Lepidoptera and Coleoptera species.

2. Description of the Prior Art

Toxic metabolites of fungi are thought to serve as chemical defense systems for the fungi that produce them, and may also be of use in protecting the food source from consumption by other organisms [see: Wicklow, In Toxigenic Fungi—Their Toxins and Health Hazards, H. Kurata et al. (ed.), Elsevier, N.Y., pp. 78–86 (1984)]. Dowd et al. [Ser. No. 201,143] disclosed that the class of fungal metabolites known as tremorgenic mycotoxins is toxic to insect species.

Many fungi produce specially adapted morphological structures called sclerotia that are critical to the long-term survival and propagation of the species [Willets, Biol. Rev. Cambridge Philos. Soc. 46:387 (1971); Gloer et al., J. Org. Chem. 53:5457–5460 (1988); Wicklow et al., Trans. Br. Mycol. Soc. 91:433 (1988)]. The factors which permit the long-term survival of sclerotia in soil are not fully understood. Many vascular plants are known to selectively allocate metabolites to important physiological structures as chemical defenses against herbivory [Herbivores: Their Interaction with Secondary Plant Metabolites, G. Rosenthal et al. (ed.), Academic, New York, (1979)]. By analogy, it has been suggested that fungal sclerotia may have evolved chemical defenses against predation by fungivorous insects which commonly encounter sclerotia in soil [Wicklow et al., supra (1988); Wicklow et al., Can. J. Bot. 60:525 (1982)]. However, aside from the sclerotia (ergot) of Claviceps spp. (which produce the ergot alkaloids), sclerotia have not been commonly explored for the production of unique, biologically active secondary metabolites. Gloer et al. [supra] and Wicklow et al. [supra (1988)] reported the isolation of four antiinsectan aflavinine derivatives that are selectively allocated to the sclerotia of Aspergillus flavus in concentrations effective against insects that encounter sclerotia under natural conditions.

SUMMARY OF THE INVENTION

We have now discovered a novel indole diterpene compound which has potent insecticidal activity. This compound, which is produced in sclerotia of the fungus Aspergillus nomius, has been given the name nominine. It has been organic solvent-extracted from the sclerotia and isolated in pure form by high-performance liquid chromatography (HPLC); its structure has been determined instrumentally. Nominine is a previously unreported structure that is related to aflavinine derivatives obtained from sclerotia of A. flavus. It is characterized by the following formula:

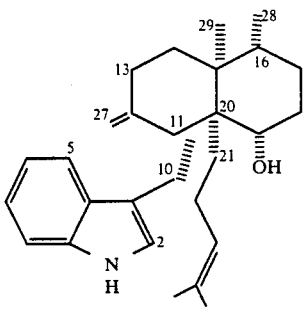

In accordance with this discovery, it is an object of the invention to introduce nominine as a novel chemical compound having insecticidal activity.

It is also an object of the invention to provide new compositions for controlling insects.

Another object of the invention is to provide an insecticide that is generated from natural renewable resources.

Other objects and advantages of this invention will become readily apparent from the ensuing description.

DEPOSIT OF BIOLOGICAL MATERIAL

A strain of the fungus, A. nomius, useful in producing nominine in accordance with the invention has been deposited under the Budapest Treaty in the Agricultural Research Service Culture Collection in Peoria, Ill., and has been assigned Deposit No. NRRL 18585. This strain of Aspergillus nomius Kurtzman, Horn & Hesseltine, sp. nov. has been characterized by Kurtzman et al., [Ant. V. Leu. 53:147 (1987)] as follows:

Colonies of Czapek's solution agar attaining a diameter of 4–7 cm in 7 days at 25° C. in 7 days restricted, 0–1.5 cm. Colony surface velvety to fluccose, consisting of white or light orange-brown vegetative mycelium and sparse to moderately abundant conidial structures, often produced in marginal areas and occasionally only after extended incubation. Conidial heads en masse yellowish citrine [XVI, R. Ridgway, Color Standards and Color Nomenclature, published by the author, Washington, D.C., 43 p. (1912)] or near warbler green [XIV, Ridgway (supra)] at 7 days, eventually shifting with age to serpentine green [XVI, Ridgway (supra)], calla green [V, Ridgway (supra)], or hellebore green [XVII, Ridgway (supra)]. Reverse light yellow- or orange-brown; red-brown exudate present in sclerotial isolates. Sclerotia dark brown to black and white-tipped, vertically elongate, indeterminate, mostly 500–800×1200–2100 μm but up to 6000 μm in length. Conidial heads biseriate or uniseriate, radiate, often splitting in to several columns, 150–600 μm in diameter; smaller heads may be loosely columnar, 20–80×100–250 μm. Conidiophores uncolored, echinulate; diameter immediately below vesicles 8–22 μm; variable in length, mostly 300–1100 μm but up to 3000 μm. Vesicles globose to subglobose, 25–65 μm diameter; metulae, 4.0–8.6×8.1–17.3 μm; phialides, 3.8–6.5×7.6–11.3 μm. Conidia globose to subglobose, echinulate; variable in diameter, 3.7–8.1 μm, mostly 4.5–6.5 μm.

Colonies on malt extract agar attaining a diameter of 4–7 cm in 7 days; growth at 42° C. in 7 days restricted, 0–.7 cm. Colony surface mostly floccose; sporulation often occurring at marginal areas. Conidial heads en masse near warbler green [IV, Ridgway (supra)], cerro green [V, Ridgway (supra)], or elm green [XVII, Ridgway (supra)]. Sclerotia when present small and less abundant than on Czapek's medium.

DETAILED DESCRIPTION OF THE INVENTION

As mentioned above, the starting material for use in this invention is the sclerotia of *A. nomius*, which is a recently identified member of the *A. flavus* taxonomic group. The sclerotia are produced by solid-substrate fermentation on corn kernels. They are prepared for extraction by grinding in a conventional manner to a suitable particle size, and then they are extracted with a nonpolar solvent, preferably hexane. The solvent extract is separated from solid material and concentrated to a light yellow oil.

Separation and purification of nominine from the crude oil can be effected by the use of conventional techniques including, for example, countercurrent distribution (CCD), column chromatography (CC), high-performance liquid chromatography (HPLC), and thin-layer chromatography (TLC). In the preferred embodiment of the invention, we have successfully employed reversed-phase semipreparative HPLC to afford pure nominine as a white powder. While not desiring to be limited thereto, the details of the separation procedure are illustrated in Example 1.

As a practical matter, it is envisioned that commercial formulations of the subject pesticidal agent would be prepared directly from fungal extracts, or fractions derived from such extracts, thereby obviating the need to isolate the compound in pure form. As indicated above, the compound is soluble in hexane; however, other suitable solvents could be readily determined by the skilled artisan. Of course, for applications demanding a high degree of specificity, that is, a high level of predictability of the intended response by both target and nontarget organisms, it would normally be preferred to prepare the formulations from pure or substantially pure nominine. For example, it is possible that extraneous substances in the natural fungal material would have an undesirable masking or antagonistic effect in regard to the intended activity, or a toxic effect toward the nontarget species.

The potency of nominine dictates that it be applied in conjunction with a suitable inert carrier or vehicle as known in the art. Of particular interest are those which are agronomically acceptable. Alcohols, ketones, esters, and aqueous surfactant mixtures are illustrative of suitable carriers. Depending on the substrate, target species, mode of application, and type of response desired, the concentration of active ingredient in the final composition may vary considerably, but typically should be at least about 1.0 ppm. Factors such as phytotoxicity toward the treated plant and tolerance of nontarget species can be used by the skilled artisan in determining the optimum level. The toxic effects of nominine on insect species are illustrated in Example 2.

Depending on the pest species, concentration of agent, and method of application, the subject compound acts to control pests by one or more mechanisms including, for instance, death inducement, growth regulation, sterilization, as well as interference with metamorphosis and other morphogenic functions. Accordingly, the level of active agent is administered in an amount effective to induce one or more of these responses as predetermined by routine testing. Where the ultimate response is pest mortality, an "effective amount" or "pesticidally effective amount" is defined to mean those quantities of agent which will result in a significant mortality rate of a test group as compared to an untreated group. The actual effective amount may vary with the species of pest, stage of larval development, the nature of the substrate, the type of vehicle or carrier, the period of treatment, and other related factors.

To be effective, the agent must be applied to the locus of, or the vicinity of, the pest to be controlled. When the agent is intended as a stomach poison, it is applied in conjunction with its carrier to the pest diet. In the case of plants, the composition will typically be applied to the leaf surfaces or else systemically incorporated. Alternatively, when the agent is to be used as contact poison, any method of topical application, such as direct spraying on the pest or on a substrate which is likely to be contacted by the pest, would be appropriate.

The compound encompassed herein is effective in controlling a variety of insects, and its toxicity is comparable to that of commercially available insecticides such as malathion and permethrin. Without desiring to be limited thereto, pests of particular interest known to be vulnerable to treatment are agronomically important insects, especially those of the orders Lepidoptera and Coleoptera.

The following examples are intended only to further illustrate the invention and are not intended to limit the scope of the invention which is defined by the claims.

EXAMPLE 1

Isolation and Purification of Nominine. Sclerotia were prepared by solid-substrate fermentation of *A. nomius,* strain NRRL 18585 [Kurtzman et al., Ant. V. Leu. 53:147 (1987)], on autoclaved corn kernels using procedures described by Wicklow et al. [supra (1988)], and were stored at 4° C. until extraction. The sclerotia (500–750 μm diameter, 53 g) were ground with a mortar and pestle and triturated 5 times with 200-ml portions of hexane. The combined hexane extracts were filtered and evaporated to afford 117 mg of a light yellow oil. The oil was subjected to reversed-phase semipreparative HPLC (5 μ $C_{18}$ column; 250×10 mm; 90:10 methanol-water at 2.0 ml/min) to afford 23.7 mg of nominine as a white powder. The retention time of the compound under these conditions was 22.2 min.

Characterization of Nominine. Nominine has: mp 54°–55° C. $[\alpha]_D$ +23.6° (c 0.85; MeOH); $^1$H NMR and $^{13}$C NMR ($CDCl_3$) data in Table I; EIMS (70 eV) 405 ($M^+$; rel. int. 57%), 387 (100), 318 (15), 304 (52), 302 (70), 288 (17), 248 (15), 232 (15), 196 (42), 180 (40), 168 (28), 156 (16); HREIMS, obs. 405.3035; calcd. for $C_{28}H_{39}NO$, 405.3031.

The molecular formula, $C_{28}H_{39}NO$, as determined by HREIMS and $^{13}$C NMR data, matched the formula of aflavinine derivatives that had been isolated earlier [Gloer et al., supra; Wicklow et al., supra (1988)], and NMR data also indicated a close similarity; but nominine contained one more double bond than the aflavinines, suggesting the presence of one less ring. Proton spin systems were established by a series of homonuclear decoupling experiments conducted in two different solvents. Carbon assignments were made on the basis of a heteronuclear C-H shift correlation experiment. Proton and carbon NMR assignments are provided in Table I. Because these data alone did not permit a conclusive structural assignment, a series of selective INEPT experiments [Bax, J. Mag. Res. 57:314 (1984)] were performed to afford long-range C-H correlations (Table II).

TABLE I

| Position | $^1H$ | $^{13}C$ |
|---|---|---|
| 1 | 7.88 (br s) | — |
| 2 | 6.93 (br s) | 121.2 (d) |
| 3 | — | 117.1 (s) |
| 4 | — | 127.7 (s) |
| 5 | 7.59 (br d; 7.8) | 118.5 (d) |
| 6 | 7.11 (dd; 7.1, 7.8) | 119.1 (d) |
| 7 | 7.17 (dd; 7.1, 8.1) | 121.8 (d) |
| 8 | 7.32 (br d; 8.1) | 111.0 (d) |
| 9 | — | 136.0 (s) |
| 10 | 3.04 (br d; 15.4) | 21.4 (t) |
|    | 3.10 (dd; 9.0, 15.4) | |
| 11 | 3.22 (br d; 9.0) | 45.9 (d) |
| 12 | — | 148.9 (s) |
| 13 | 2.11 (ddd; 3.2, 3.5, 12.7) | 33.5 (t) |
|    | 2.21 (m) | |
| 14 | 1.51 (m) | 34.4 (t) |
|    | 1.68 (m) | |
| 15 | — | 40.9 (s) |
| 16 | 2.45 (m) | 31.1 (d) |
| 17 | 1.33 (m) | 25.4 (t) |
|    | 1.70 (m) | |
| 18 | 1.64 (m) | 28.8 (t) |
|    | 1.92 (m) | |
| 19 | 4.52 (br s) | 70.0 (d) |
| 20 | — | 47.9 (s) |
| 21 | 1.36 (m) | 29.2 (t) |
|    | 1.75 (m) | |
| 22 | 2.21 (m) | 23.9 (t) |
| 23 | 5.17 (br t; 7.1) | 125.8 (d) |
| 24 | — | 131.2 (s) |
| 25 | 1.67 (br s) | 17.8 (q) |
| 26 | 1.71 (br s) | 25.8 (q) |
| 27 | 4.81 (br s) | 107.7 (t) |
|    | 4.92 (br s) | |
| 28 | 1.01 (s) | 18.7 (q) |
| 29 | 0.82 (d; 6.6) | 16.6 (q) |

Data recorded in $CHCl_3$ at 360 and 90.7 MHz, respectively.

TABLE II

| Proton Signal Irradiated | Carbon Signals Observed |
|---|---|
| H-2 | 117.0 (C-3), 127.7 (C-4), 135.9 (C-9) |
| H-5 | 117.0 (C-3) |
| H-10 | 121.2 (C-2), 148.9 (C-12) |
| H-11 | 29.2 (C-21), 47.9 (C-20), 107.7 (C-27), 148.9 (C-12) |
| H-16 | 16.6 (C-29), 18.7 (C-28), 40.9 (C-15) |
| H-19 | 40.9 (C-15) |
| H-23 | 17.8 (C-25), 23.8 (C-22), 25.8 (C-26), 29.2 (C-21) |
| H-26 | 125.8 (C-23), 131.2 (C-24) |
| H-27 | 33.5 (C-13), 45.9 (C-11) |
| H-28 | 31.1 (C-16), 34.4 (C-14), 40.9 (C-15), 47.9 (C-20) |
| H-29 | 25.4 (C-17), 31.1 (C-16), 40.9 (C-15) |

The presence of the following partial structure

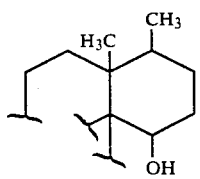

was established by the results of proton NMR decoupling experiments and by comparison of the NMR data to those obtained for the aflavinines [Gloer et al., supra]. Confirmation of this obtained by long-range correlation of $H_3$-29 with C-15, 16, and 17, and correlation of $H_3$-28 with C-14, 15, 16, and 20. The presence of a 3-substituted indole moiety, a 4-methyl-3-butenyl group, a downfield-shifted, isolated —CHCH$_2$— unit, and an exo methylene group was also clearly indicated by proton NMR decoupling experiments and carbon NMR data. Three key observations resulting from selective INEPT experiments were instrumental in establishing the connectivity of these units. The geminal protons of the exo methylene unit were correlated with the CH carbon of the —CHCH$_2$— unit and the terminal CH$_2$ carbon of the above partial structure (C-11 and C-13, respectively). In addition, one of the H-10 protons was correlated with C-2 of the indole unit and the disubstituted carbon of the exo methylene group (C-12), suggesting the gross structure (supra) for nominine. Finally, the proposed location of the 4-methyl-3-butenyl group was confirmed by correlation of H-11 with carbons 12, 20, 21, and 27.

The relative stereochemistry shown for nominine was assigned as shown based on its close biogenetic relationship to the aflavinines. Support for this analogy was provided by comparison of parallel NMR data for nominine with those of the aflavinines, and by analysis of NOESY and difference NOE experiments. For example, NOESY data indicated that H-9, H-5, and H-27 are all spatially close to H$_2$-10, while irradiation of H-16 in a difference NOE experiment enhanced the signal for H-11. Additional correlations were also consistent with the proposed relative stereochemistry.

EXAMPLE 2

Insecticidal Activity of Nominine. The compound was evaluated by insect bioassays described previously in Dowd [Entomol. Exp. Appl. 47:69 (1988)]. Neonate larvae of *H. zea* and second instar (ca. 0.75 mg) larvae of *C. hemipterus* were used for all assays. They were obtained from laboratory colonies reared on pinto bean-based diet at 27°±1° C., 40±10% relative humidity, and a 14:10 light:dark photoperiod.

The diet used to rear the insects was based on a standard pinto bean diet for many species, which contains the following ingredients: 120 g dried pinto beans, 43 g wheat germ, 28 g brewer's yeast, 8 g Vanderzant's vitamin mix, 2.8 g ascorbic acid, 1.75 g methyl paraben, 0.9 g sorbic acid, 12 g agar, 2 ml formaldehyde (38%), 1.5 ml of propionic-phosphoric acid solution (42% propionic acid, 4.2% phosphoric acid), and 550 ml water. All dry diet ingredients (except for the pinto beans) were purchased from U.S. Biochemicals Corp. Before use, the beans were soaked in water until saturated (overnight). The agar was added to 250 ml of water and brought to a boil. The other ingredients were blended in a Waring blender until uniformly mixed. The hot agar was added, and blending continued until all ingredients were uniformly mixed.

The pinto bean-based diet thus prepared was added in 5-ml quantities to test tubes. The test tubes were held at 60° C. until chemicals were incorporated to prevent solidification of the diet. The nominine was added in 125 μl of acetone to the liquid diet to give a final concentration of 25 ppm. Upon addition of the nominine, the mixture was removed from the water bath. The chemical was incorporated into the diets by blending vigorously with a vortex mixer for 20 sec. Preliminary observations with colored solutions of both water and acetone indicated uniform incorporation by this method. The diets were dispensed into culture plates and allowed to cool to room temperature. To remove the potentially toxic acetone, the diets were placed in a fume hood for ca. 20 min until slight darkening occurred. The diets were cut into approximately equal sections, and each section was placed into a well of a 24-well immunoassay plate. A single neonate *H. zea* or 5 C. hemipterus larvae [Wicklow et al., supra (1988)] was added to each well. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 2, 4, and 7 days, and the surviving larvae were weighed after 7 days. Each chemical set was tested on a total of 40 larvae. Diet feeding rating for C. hemipterus larvae was based on a scale of 1 (limited to no feeding) to 4 (diet thoroughly tunneled of pulverized [Wicklow et al., supra (1988)].

Nominine exhibited potent activity against the widespread crop pest, corn earworm (*Heliothis zea*), where it caused 38% mortality (vs. 10% control) and 97% reduction in growth weight (2 mg vs. 59 mg for controls) of insects surviving for 7 days, when incorporated into a standard diet at 25 ppm. Thus, nominine was substantially more effective than rotenone in this assay, and exhibited activity comparable to that of permethrin, a potent synthetic insecticide. It also caused reduction in growth of dried-fruit beetle larvae, *Carpophilus hemipterus*, (1.3 mg vs. 1.8 mg control increase in weight) and in feeding (diet rating of 2.25 vs. 4.0 for control).

It is understood that the foregoing detailed description is given merely by way of illustration and that modification and variations may be made therein without departing from the spirit and scope of the invention.

We claim:

1. A substantially pure indole diterpene designated nominine and having the structure:

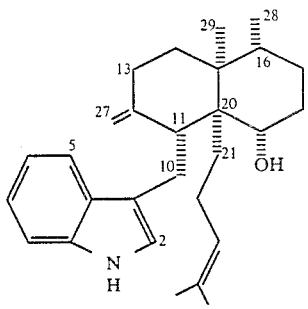

2. A composition for controlling insects comprising an insecticidally effective amount of nominine and a inert carrier.

3. A method for controlling insects comprising applying to a locus of said insects an insecticidally effective amount of nominine.

4. The method as described in claim 3 wherein said insects are Lepidoptera species.

5. The method as described in claim 3 wherein said insects are *Heliothis zea*.

6. The method as described in claim 3 wherein said insects are Coleoptera species.

7. The method as described in claim 3 wherein said insects are *Carpophilus hemipterus*.

* * * * *